United States Patent [19]

Manning et al.

[11] Patent Number: 5,055,448

[45] Date of Patent: Oct. 8, 1991

[54] LINEAR DERIVATIVES OF ARGININE VASOPRESSIN ANTAGONISTS

[75] Inventors: Maurice Manning, Toledo, Ohio; Wilbur H. Sawyer, Scarsdale, N.Y.

[73] Assignees: Medical College of Ohio, Toledo, Ohio; Trustees of Columbia University, New York, N.Y.; a part interest

[21] Appl. No.: 66,949

[22] Filed: Jun. 25, 1987

[51] Int. Cl.$^5$ .................. A61K 37/34; C07K 7/16
[52] U.S. Cl. .................................. 514/16; 530/315; 530/317; 530/328; 530/329; 514/807
[58] Field of Search .............. 530/328, 329, 315, 317; 514/15, 14, 16, 807

[56] References Cited

U.S. PATENT DOCUMENTS

| | | | |
|---|---|---|---|
| 3,415,805 | 10/1968 | Siedel et al. | 530/315 |
| 4,285,858 | 8/1981 | Cort et al. | 530/315 |
| 4,367,225 | 1/1983 | Manning et al. | 530/315 |
| 4,399,125 | 8/1983 | Manning et al. | 530/315 |
| 4,469,679 | 9/1984 | Huffman et al. | 530/315 |
| 4,504,469 | 3/1985 | Melin et al. | 530/328 |
| 4,542,124 | 9/1985 | Huffmann et al. | 530/328 |
| 4,543,349 | 9/1985 | Callahan et al. | 530/315 |
| 4,551,445 | 11/1985 | Manning et al. | 530/315 |
| 4,597,901 | 7/1986 | Yim | 530/328 |
| 4,656,248 | 4/1987 | Kalbag et al. | 530/315 |
| 4,684,716 | 8/1987 | Yim | 530/328 |
| 4,714,696 | 12/1987 | Manning et al. | 530/315 |

FOREIGN PATENT DOCUMENTS

| | | | |
|---|---|---|---|
| 1113267 | 7/1965 | United Kingdom | 530/315 |
| 2122622 | 1/1984 | United Kingdom | 530/315 |

OTHER PUBLICATIONS

Houby et al., The Peptides, 1987, pp. 77–207, chap. 4.
Rekowski et al., Act a Chemica Scandivanian (1985), p. 453–457.
Zadoral et al., Collection Ozeckoslov Chem. Comm., vol. 37, 1972, pp. 1539–1545.
Manning et al., Neurokypophysis, 1977, pp. 9–21.
Jost et al., Handbook of Neurohypophysical Hormone Analogs, vol. 1, part 2, pp. 163–165.
Sawyer et al., Ann. Rev. Pharmacology, vol. 13, p. 5–17.
Manning et al., Nature, vol. 329, 1987, pp. 839–840.
Manning et al., Int. J. Peptide Protein Res., 32, 1988, pp. 455–467.
Chan et al., Science, vol. 161 (1968) at 280.
Chan et al., pi J. Pharmacol. Exp. Ther., vol. 174 (1970) at 541.
Chan et al., pi J. Pharmacol. Exp. Ther., vol. 196 (1976) at 746.
Dousa et al., Science, vol. 167 (1970) at 1134.
Nestor et al., *J. Med. Chem., vol. 18 (1975) at 1022.*
Larsson et al., J. Med. Chem., vol. 21 (1978) at 352.
Sawyer et al., Science, vol. 212 (1981) at 49.
Manning et al., J. Med. Chem., vol. 24 (1981) at 701.
Manning et al., J. Med. Chem., vol. 28 (1985) at 1485.
Manning et al., "Studies Leading to Orally Active Antagonists of the Antidiuretic (V$_2$) and Vasopressor (V$_1$) Responses to Arginine Vasopressin", Proc. 9th Amer. Pep. Symp., Hruby et al., eds., Pierce Chemical Co., Rockford, IL (1985) at 599–602.
Manning et al., J. Med. Chem., vol. 26 (1983) at 1607.
Sawyer et al., Molecular and Cellular Endocrinology, vol. 22 (1981), 117–134.
Manning et al., The Pituitary, Beardwell et al., eds., Butterworths, Kent, England (1981), 265–296.
Manning et al., "Peptides, Synthesis, Structure, Function", Rich et al., eds., Pierce Chemical Co. (1981) at 257–260.
Manning et al., J. Med. Chem., vol. 25 (1982) at 45.
Manning et al., J. Med. Chem., vol. 25 (1982) at 414.
Lebl et al., Peptides, Walter de Gruyter & Co., Berlin (1983) at 457.
Simek et al., Peptides, Walter de Gruyter & Co., Berlin (1983) at 461.
Gazis et al., Peptides, Walter de Gruyter & Co., Berlin (1983) at 465.
Buku et al., Int. J. Peptide Protein Res., vol. 23 (1984) at 551.
Brtnik et al., Coll. Czech. Chem. Comm., vol. 48 (1983) at 2862.
Toth et al., Acta Physica et Chimica, vol. 29 (1983) at 187.
Huffman et al., J. Med. Chem., vol. 28 (1985) at 1759.

(List continued on next page.)

Primary Examiner—John Doll
Assistant Examiner—T. D. Wessendorf
Attorney, Agent, or Firm—Emch, Schaffer, Schaub & Porcello

[57] ABSTRACT

Compounds acting as antagonists of the antidiuretic-/and or vasopressor activity of arginine vasopressin are those of the formula

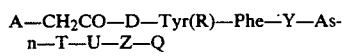

A—CH$_2$CO—D—Tyr(R)—Phe—Y—Asn—T—U—Z—Q wherein A is a-adamantyl, cyclohexyl, cyclopentyl, 1-mercaptocyclohexyl, 1-mercaptocyclopentyl, 1-ethyl-1-mercaptopropyl, yclohexylmethyl, cyclopentylmethyl, methyl, isopropyl, tert-butyl or phenyl; R is alkyl of 1-4 carbon atoms; Y is Val, Ile, Thr, Ala, Lys, Cha, Nva, Met, Nle, Orn, Ser, Asn, Gln, Phe, Tyr, Gly, Abu or Leu; T is Pen, Abu, Orn, Oys, Arg, Ala, Cha or Thr; U is Pro, Arg, Lys or Orn or a single bond; Z is (d-or L-) Arg, Orn or Lys and Q is Gly(NH$_2$), Arg(NH$_2$), Orn(NH$_2$), Lys (NH$_2$), (D- or L-)Ala(NH$_2$), Ser(NH$_2$), Val(NH$_2$), Phe(NH$_2$), Ile(NH$_2$), Thr(NH$_2$), Pro(NH$_2$), Tyr(NH$_2$), NH$_2$, OH, NHR, NGbzl, NH(CH$_2$)$_p$NH$_2$ or NH(CH$_2$)$_p$OH, wherein R is as above and p is an integer from 2 to 6. Compounds wherein T is Cys have similar activity.

15 Claims, No Drawings

OTHER PUBLICATIONS

Manning et al., *Nature*, vol. 308 (1984) at 652.
Berde et al., "Handbook of Experimental Pharmacology", O. eichler et al., eds., Springer-Verlag, Berlin, vol. XXIII (1968) at 862.
Huffman et al., "reverse Turn Mimics", Tenth American Peptide Symposium Abstract No. LS13, St. Louis, MO, May 23-28, 1986.
Moore et al., "Vasopressin Agonists and Antagonists Present Distinct Pharmacophores at the Renal $V_2$ Receptor", Tenth American Peptide Symposium Abstract No. LW5, St. Louis, MO, May 23-28, 1987.
Callahan et al., "Synthesis of a Vasopressin Antagonists Incorporating the Novel Amino Acid 6,6-Cyclopentamethylene-2-Aminosuberic Acid as a Disulfide Replacement", Tenth American Peptide Symposium Abstract No. P-27, St. Louis, MO, May 23-28, 1987.
El-Fehail Ali et al., "Potent Vasopressin Antagonists Modified at the Carbosy-Terminal Tripeptide Tail", Tenth American Peptide Symposium Abstract No. P-96, St. Louis, MO, May 23-28, 1987.
Bryan et al., "Vasopressin Antagonist Analogs Containing glutamine at Position 7 and 8", Tenth american Peptide Symposium Abstract No. P-103, St. Louis, MO, May 23-28, 1987.
Huffman et al., "Dicarba Analogs of Vasopressin Antagonists Exhibit Reduced Partial Agonist Activity and Retain Full Antagonist Potency", Tenth American Peptide Symposium Abstract No. P-127, St. Louis, MO, May 23-28, 1987.
Debrosse et al., "Conformational Mobility of a Vasopressin antagonist Analog", Tenth American Peptide Symposium Abstract No. P-192, St. Louis, MO, May 23-28, 1987.
The Peptides, Chapter 4, Editor Clark W. Smith, 1987, Academic Press, Inc.
Bankowski et al., 21 *J. Med. Chem.*, 850 (1978).
Shculz et al., 10 *J. Med. Chem.*, 1037 (1967).
Schulz et al., 9 *J. Med. Chem.*, 647 (1966).
Hruby et al., 22 *J. Med. Chem.*, 7 (1979).
Vavrek et al., 15 *J. Med. Che.*, 123 (1972).
Manning et al., 21 *J. Med. Chem.*, 79 (1978).

LINEAR DERIVATIVES OF ARGININE VASOPRESSIN ANTAGONISTS

The invention described herein was made in the course of work under a grant or award from the Department of Health and Human Services.

BACKGROUND OF THE INVENTION

This invention relates to novel linear peptides which antagonize the antidiuretic and/or vasopressor action of arginine vasopressin in vivo.

PRIOR ART STATEMENT

Attempts to develop clinically useful synthetic antagonists of in vivo antidiuretic and/or vasopressor responses to arginine vasopressin, the antidiuretic hormone (ADH), have led to the synthesis and pharmacological evaluation of hundreds of analogs of the neurohypophysial peptides, oxytocin and vasopressin.

Analogs of vasopressin or oxytocin which antagonize antidiuretic responses to ADH have been reported by Chan et al., *Science*, vol. 161 (1968) at 280 and *J. Pharmacol. Exp. Ther.*, vol. 174 (1970) at 541 and vol. 196 (1976) at 746; Dousa et al., *Science*, vol. 167 (1970) at 1134; Nestor et al., *J. Med. Chem.*, vol. 18 (1975) at 1022 and Larsson et al., *J. Med. Chem.*, vol. 21 (1978) at 352, herein incorporated by reference. None of the compounds reported has been pharmacologically or clinically useful as an antidiuretic antagonist.

The synthesis and evaluation of vasopressin analogs, incorporating etherified tyrosine at the 2-position, valine at the 4-position and D- or L-arginine at the 8-position, which antagonize the antidiuretic action of ADH in vivo, have been reported by Sawyer et al., *Science*, vol. 212 (1981) at 49; Manning et al., *J. Med. Chem.*, vol. 24 (1981) at 701 and vol. 28 (1985) at 1485; and Manning et al., U.S. Pat. Nos. 4,367,225 and 4,399,125, herein incorporated by reference.

The synthesis of arginine vasopressin derivatives, containing unetherified tyrosine at the 2-position, has been described by Manning et al., "Studies Leading to Orally Active Antagonists of the Antidiuretic ($V_2$) and Vasopressor ($V_1$) Responses to Arginine Vasopressin," *Proc. 9th Amer. Pep. Symp.*, Hruby et al., eds., Pierce Chemical Co., Rockford, Ill. (1985) at 599-602.

The effect of variation in the amino acid at the 4-position of arginine vasopressin antagonists has been investigated by Manning et al., *J. Med. Chem.*, vol. 26 (1983) at 1607 and in U.S. Pat. No. 4,551,445.

Design of tissue-specific agonists and antagonists in the field of neurohypophysial peptides has been considered by Sawyer et al., *Molecular and Cellular Endocrinology*, vol. 22 (1981), 117-134; Manning et al., "*The Pituitary*," Beardwell et al., eds., Butterworths, Kent, England (1981), 265-296; Manning et al., "Peptides, Synthesis, Structure, Function," Rich et al., eds., Pierce Chemical Co., (1981) at 257-260 and Manning et al., *J. Med. Chem.*, vol. 25 (1982) at 45 and 414.

Modification of oxytocin, containing a D-amino acid at the 2-position has been disclosed by Lebl et al., *Peptides*, Walter de Gruyter & Co., Berlin (1983), at 457. Other modifications, having a penicillamine unit at the 1- and 6-positions of vasopressin, have been disclosed by Simek et al., ibid, at 461. Modification of vasopressin analogs at the 9-position, for example, 1-deamino[9-D-alaninamide]AVP, has been investigated by Gazis et al., ibid., at 465. In the latter article, retention of significant antidiuretic activity of vasopressins, having 9-(D- or L-) alaninamide groups is recited, but the compounds have markedly decreased pressor activity. See also Buku et al., *Int. J. Peptide Protein Res.*, vol. 23 (1984), at 551.

Brtnik et al., *Coll. Czech. Chem. Comm.*, vol. 48 (1983) at 2862 disclose modification of vasopressin by removal of glycine at the 9-position and replacement of D-Arg at the 8-position by basic non-coded amino acids. These compounds have almost no uterotonic, pressor or antidiuretic activity. Toth et al., *Acta Physica et Chimica*, vol. 29 (1983) at 187, report the synthesis of three analogues of deamino-vasopressin, lacking the C-terminal glycinamide group. Cort et al. have proposed, in U.S. Pat. No. 4,285,858, that vasopressin analogs having a configuration of L—Arg—D—AlaNH$_2$ or D—Arg—L—AlaNH$_2$ at the 8- or 9-positions have very weak antidiuretic or pressor activity.

Huffman et al. (U.S. Pat. No. 4,469,679) recite the preparation of octapeptide vasopressin antagonists. Callahan et al. have proposed the synthesis of heptapeptide analogues in U.S. Pat. No. 4,543,349. Related compounds are disclosed by Huffman et al., *J. Med. Chem.*, vol. 28 (1985) at 1759.

However, Manning et al., *Nature*, vol. 308 (1984) at 652, have found that the carboxy terminus of vasopressin is required for agonist activity, but not for binding.

Berde et al., "Handbook of Experimental Pharmacology," O. Eichler et al., eds., Springer-Verlag, Berlin, vol. XXIII (1968) at 862, have recited that modifications of oxytocin and vasopressin which eliminate the two sulfur atoms and open the ring, or which enlarge the ring, cause almost complete deactivation.

It is therefore apparent that the correlation between structure of neurohypophysial peptides and action in vivo is not well understood and there is a continuing need for the development of pharmacologically and clinically effective antagonists of the antidiuretic action of arginine vasopressin.

OBJECT OF THE INVENTION

It is the object of the invention to provide novel antagonists of the antidiuretic and/or vasopressor action of ADH, which are effective in vivo.

SUMMARY OF THE INVENTION

This invention relates to novel antagonists of the antidiuretic and/or vasopressor action of ADH, which are compounds of the General Formula:

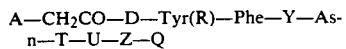

A—CH$_2$CO—D—Tyr(R)—Phe—Y—Asn—T—U—Z—Q wherein A is 1-adamantyl, cyclohexyl, cyclopentyl, 1-mercaptocyclohexyl, 1-mercaptocyclopentyl, 1-ethyl-1-mercaptopropyl, cyclohexylmethyl, cyclopentylmethyl, methyl, isopropyl, tert-butyl or phenyl; R is alkyl of 1-4 carbon atoms; Y is Val, Ile, Thr, Ala, Lys, Cha, Nva, Met, Nle, Orn, Ser, Asn, Gln, Phe, Tyr, Gly, Abu or Leu; T is Pen, Abu, Orn, Lys, Arg, Ala, Cha or Thr; U is Pro, Arg, Lys or Orn or a single bond; Z is (D- or L-)Arg, Orn or Lys; Q is Gly(NH$_2$), Arg(NH$_2$), Orn(NH$_2$), Lys(NH$_2$), Ser(NH$_2$), (D- or L-)Ala(NH$_2$), Val(NH$_2$), Phe(NH$_2$), Ile(NH$_2$), Thr(NH$_2$), Pro(NH$_2$), Tyr(NH$_2$), NH$_2$, OH, NH(CH$_2$)$_p$NH$_2$, NH(CH$_2$)$_p$OH, NHR or NHbzl, wherein R is as above and p is an integer from 2 to 6.

This invention further relates to a method for antagonizing the in vivo antidiuretic and/or vasopressor response to ADH, comprising administering to an animal being treated an amount of a compound of the General Formula, in admixture with a physiologically and pharmaceutically acceptable carrier, effective to antagonize the antidiuretic and/or vasopressor response to ADH.

In another aspect, this invention relates to a method for antagonizing the in vivo antidiuretic and/or vasopressor response to ADH, comprising administering to an animal being treated an amount of a compound, otherwise as in the General Formula, wherein T is Cys, in admixture with a physiologically and pharmaceutically acceptable carrier, effective to antagonize the antidiuretic and/or vasopressor response to ADH.

DETAILED DESCRIPTION

Compounds of the invention are linear derivatives of arginine vasopressin. Amino acids are in the L-form, unless otherwise indicated. Each symbol, except for that of the 9-terminal substituent, is for the acyl (—C=O—) residue of the designated amino acid. For example, 9—OH represents a compound with a completed —COOH group of the amino acid residue at the 8-position and is, therefore, a desglycinamide compound. Unless otherwise indicated, the abbreviations for the amino acids are those used in *J. Biol. Chem.*, vol. 256 (1981), beginning at 1.

In the specification and claims:

Aaa means (1-adamantyl)acetyl

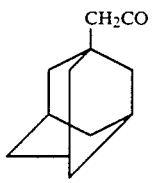

(1-mercaptocyclohexyl)acetyl or $d(CH_2)_5(SH)$ means

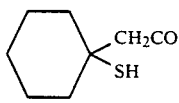

$dEt_2(SH)$ or (3-ethyl-3-mercapto)valeroyl means $(C_2H_5)_2C(SH)CH_2CO$ and

Pa or propionyl means $CH_3CH_2CO$.

The correlation between full names and abbreviations is accordingly:

Aaa-D-Tyr(Et)-Phe-Val-Asn-Abu-Pro-ArgNH$_2$, (1-adamantyl)acetyl-D-(O-ethyl)tyrosyl-phenylalanyl-valyl-asparaginyl-(2-amino)butyryl-prolyl-argininamide;

Aaa-D-Tyr(Et)-Phe-Val-Asn-Orn-Pro-ArgNH$_2$, (1-adamantyl)acetyl-D-(O-ethyl)tyrosyl-phenylalanyl-valyl-asparaginyl-ornithyl-prolyl-argininamide;

Aaa-D-Tyr(Et)-Phe-Val-Asn-Lys-Pro-ArgNH$_2$, (1-adamantyl)acetyl-D-(O-ethyl)-tyrosyl-phenylalanyl-valyl-asaparaginyl-lysyl-prolyl-argininamide;

Aaa-D-Tyr(Et)-Phe-Val-Asn-Arg-Pro-ArgNH$_2$, (1-adamantyl)acetyl-D-(O-ethyl)tyrosyl-phenylalanyl-valyl-asparaginyl-arginyl-prolyl-argininamide;

$d(CH_2)_5(SH)$-D-Tyr(Et)-Phe-Val-Asn-Cys-Pro-ArgGlyNH$_2$, (1-mercaptocyclohexyl)acetyl-D-(O-ethyl)-tyrosyl-phenylalanyl-valyl-asparaginyl-cysteinyl-prolyl-arginyl-glycinamide;

$d(CH_2)_5(SH)$-D-Tyr(Et)-Phe-Val-Asn-Abu-Pro-ArgGlyNH$_2$, (1-mercaptocyclohexyl)acetyl-D-(O-ethyl)-tyrosyl-phenylalanyl-valyl-asparaginyl-(2-amino)butyryl-prolyl-arginyl-glycinamide;

$dEt_2(SH)$-D-Tyr(Et)-Phe-Val-Asn-Abu-Pro-ArgGlyNH$_2$, (3-ethyl-3-mercapto)valeroyl-D-(O-ethyl)-tyrosyl-phenylalanyl-valyl-asparaginyl-(2-amino)butyryl-prolyl-arginyl-glycinamide;

Aaa-D-Tyr(Et)-Phe-Val-Asn-Abu-Pro-Arg-GlyNH$_2$, (1-adamantyl)acetyl-D-(O-ethyl)tyrosyl-phenylalanyl-valyl-asparaginyl-(2-amino)butyryl-prolyl-arginyl-glycinamide;

Aaa-D-Tyr(Et)-Phe-Val-Asn-Abu-Pro-ArgNHCH$_2$NH$_2$NH$_2$, (1-adamantyl)acetyl-D-(O-ethyl)tyrosyl-phenylalanyl-valyl-asparaginyl-(2-amino)butyryl-prolyl-arginine-N-(2-aminoethyl)amide Aaa-D-Tyr(Et)-Phe-Val-Asn-Abu-Pro-Arg-AlaNH$_2$, (1-adamantyl)acetyl-D-(O-ethyl)tyrosyl-phenylalanyl-valyl-asparaginyl-(2-amino)butyryl-prolyl-arginyl-alaninamide;

Aaa-D-Tyr(Et)-Phe-Val-Asn-Abu-Pro-Arg-ArgNH$_2$, (1-adamantyl)acetyl-D-(O-ethyl)tyrosyl-phenylalanyl-valyl-asparaginyl-(2-amino)butyryl-prolyl-arginyl-argininamide;

Aaa-D-Tyr(Et)-Phe-Val-Asn-Abu-Pro-D-Arg-ArgNH$_2$, (1-adamantyl)acetyl-D-(O-ethyl)tyrosyl-phenylalanyl-valyl-asparaginyl-(2-amino)butyryl-prolyl-D-arginyl-argininamide and Pa-D-Tyr(Et)-Phe-Val-Asn-Abu-Pro-Arg-ArgNH$_2$, propionyl-D-(O-ethyl)tyrosyl-phenylalanyl-valyl-asparaginyl-(2-amino)butyryl-prolyl-arginyl-argininamide.

The active peptides were synthesized by solid phase synthesis, as described by Bankowski et al. (1978), infra; Merrifield, *J. Am. Chem. Soc.*, vol. 85 (1963) at 2149 and *Biochemistry*, vol. 3 (1964) at 1385; Manning, *J. Am. Chem. Soc.*, vol. 90 (1968) at 1348; Manning et al., *J. Med. Chem.*, vol. 19 (1976) at 376; Lowbridge et al., *J. Med. Chem.*, vol. 20 (1977) at 1173; Manning et al., *J. Med. Chem.*, vol. 16 (1973) at 975; Kruszynski et al. (1980), infra; Sawyer et al., (1981), supra or Manning et al. (1981), supra.

Compounds of the 9-desglycinamide group, that is, Q is NH$_2$, NH(CH$_2$)$_p$NH$_2$, NH(CH$_2$)$_q$OH or the the like, are prepared as for other arginine vasopressin derivatives, except that one less cycle of deprotection, neutralization and coupling is employed. That is, the first amino acid residue, attached to resin, will be (D- or L-) Arg, for example, rather than Gly, as would be the case for compounds in which Q is to be GlyNH$_2$. Cleavage is carried out by methods in the literature, using the appropriate amine or diamine. See Manning, supra, or Glass et al., *J. Med. Chem.*, vol. 16 (1973), page 160, for example.

It will be understood that compounds in which U is a single bond are octapeptides. Compounds in which U and Z are amino acids and Q is other than an aminoacid amide are also octapeptides. However, compounds having terminal alkylene diamine functions can also be considered to be the next higher peptide, since the length of the alkylene chain corresponds sterically to an additional peptide linkage.

Compounds in which the amino acid at the 9-position is other than Gly(NH$_2$) are prepared in a similar fashion, but by attaching an amino acid other than glycine to the resin at the start of the synthesis. An alternative approach to these compounds was by cleavage of a protected octapeptide resin with HBr/TFA as described by Walter et al., *J. Med. Chem.*, vol 19 (1976) at 376. After purification of the resulting intermediate, the desired protected nonapeptide was obtained by an 8+1 coupling in solution.

Desglycinamide compounds, that is Q is OH, in accordance with this invention are prepared as described in the examples.

Preparation of the uncyclized 6-cysteine compounds of this invention differs from the prior art, particularly that of Example 3 of Manning et al. '225, supra, as follows: the oxidative cyclization step normally carried out is omitted, allowing the isolation and purification of the disulfhydryl compounds.

The discovery of the antidiuretic antagonists d(CH$_2$)$_5$Tyr(alk)VAVP, Sawyer et al. (1981), supra, and Manning et al. (1981), supra, led to the synthesis of various analogs having a cyclopentamethylene ring structure and various substituents at the 2-position. Other modifications at the 4-, 6-, 7-, 8- and 9-positions, have been proposed.

It will also be understood that the R substituents on tyrosine and the nitrogen of the terminal amide function can be linear or branched and contemplated equivalents include all possible isomers. In the specification and claims, "bzl" means benzyl.

Compounds of this invention, having an action antagonistic toward the antidiuretic action of arginine vasopressin, are generally those wherein the 2-substituent is an ether of D-tyrosine and the 4-substituent is an aliphatic amino acid.

Most of compounds of the General Formula are accordingly very effective antagonists of the antidiuretic response to ADH. They can therefore be used in pharmacological studies on the contribution of ADH to a variety of pathological states involving water retention. It is further contemplated that they could be effective and specific agents for treating the syndrome of inappropriate secretion of ADH, that is, the Schwartz-Bartter syndrome or SIADH. This syndrome can complicate a number of disorders, including carcinomas, pulmonary diseases, intracranial diseases and head injuries, Bartter et. al., *Am. J. Med.*, vol. 42 (1967) at 790. In addition, compounds of the General Formula are effective as antagonists of the vasopressor response to ADH.

Surprisingly, activity of the compounds of the invention as antagonists of ADH or vasopressin is not lost although the compounds of this invention are linear and do not have the 1-6-disulfide function, characteristic of vasopressin and oxytocin. In addition, antagonistic activity is retained and enhanced by substituting other amino acids for cysteine in the 6-position.

The compounds of this invention can be employed in mixtures with conventional excipients, i.e., physiologically and pharmaceutically acceptable organic or inorganic carriers suitable for parenteral or other application, provided that the carriers do not interact deleteriously with the active compounds.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing the osmotic pressure, buffers, coloring, flavoring and/or aromatic substances, which do not deleteriously interact with the active compounds.

For parenteral or intranasal application, solutions, preferably aqueous solutions, as well as suspensions, emulsions or implants, including suppositories, are particularly suitable. Ampoules are convenient unit dosages.

For enteral application, particularly suitable are tablets, dragees, or capsules, having talc and/or a carbohydrate carrier or binder or the like, the carrier preferably being lactose and/or corn starch and/or potato starch. A syrup, elixir or the like can be used, wherein a sweetened vehicle is employed. Sustained release compositions can be formulated, including those wherein the active compound is protected with differentially degradable coatings, e.g., by microencapsulation, multiple coatings, etc.

The compounds of the General Formula are generally administered to animals, including but not limited to mammals, e.g., livestock, household pets, humans, cattle, cats and dogs. A diuretically effective daily dosage of the active compounds can be adminstered parenterally in a single dosage or as divided dosages throughout the day.

Parenteral or intranasal administration is preferred. The compounds of this invention are particularly valuable in the treatment of humans afflicted with water retention of any etiology. In this regard, they can be administered in substantially the same manner as the known compounds oxytocin and vasopressin, to achieve their physiological effects.

It will be appreciated that the actual preferred amounts of active compounds used will vary according to the specific compound being utilized, the particular compositions formulated, the mode of application, and the particular organisms being treated. Optimal application rates under/in a given set of conditions can be ascertained by those skilled in the art of using conventional dosage determination tests in view of the above guidelines.

DESCRIPTION OF PREFERRED EMBODIMENTS

Preferred octapeptide antidiuretic antagonists of this invention are those wherein:
(a) A is 1-adamantyl;
(b) R is ethyl, including (a);
(c) R is methyl, including (a);
(d) Y is Val, including each of (a)-(c);
(e) T is Abu, including each of (a)-(d);
(f) T is Orn, including each of (a)-(d);
(g) T is Lys, including each of (a)-(d);
(h) T is Arg, including each of (a)-(d);
(i) U is Pro, including each of (a)-(h);
(j) Z is Arg, including each of (a)-(i);
(k) Q is NH$_2$, including each of (a)-(j) and
(l) Q is NHCH$_2$CH$_2$NH$_2$, including each of (a)-(j).

Most preferred among the octapeptides are compounds in which A is 1-adamantyl; R is ethyl; Y is Val; U is Pro; Z is Arg; Q is NH$_2$ and T is Orn, Lys or Arg.

Among the nonapeptides of this invention, preferred compounds are those wherein:
(a) A is 1-adamantyl;
(b) A is 1-ethyl-1-mercaptopropyl;
(c) A is 1-mercaptocyclohexyl;
(d) A is methyl;
(e) R is ethyl, including each of (a)-(d);
(f) R is methyl, including each of (a)-(d);
(g) Y is Val, including each of (a)-(f);
(h) T is Abu, including each of (a)-(g);
(i) U is Pro, including each of (a)-(h);
(j) Z is Arg, including each of (a)-(i);
(k) Z is D-Arg, including each of (a)-(i);
(l) Q is GlyNH$_2$, including each of (a)-(k);
(m) Q is AlaNH$_2$, including each of (a)-(k) and
(n) Q is ArgNH$_2$, including each of (a)-(k).

Most preferred nonapeptides are those wherein A is 1-adamantyl, R is ethyl, Y is Val, T is Abu, U is Pro, Z is (D- or L-)Arg and Q is ArgNH$_2$.

Preferred compounds, otherwise of the General Formula, except that T is Cys, are those wherein A is 1-adamantyl, cyclohexyl, cyclopentyl, cyclohexylmethyl, cyclopentylmethyl, methyl, isopropyl, tert-butyl or phenyl.

Without further elaboration, it it believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Chloromethylated resin (Bio-Rad Bio-Beads SX-1) was esterified by the procedure of Gisin, *Helv. Chim. Acta.*, vol. 56 (1973) at 1476 with Boc-Gly, for example. Amino acid derivatives, including Boc-D-Tyr(Me), Boc-Tyr(Et), BocOrn(Tos) and the like, were supplied by Bachem or synthesized. 1-Adamantylacetic acid (C$_{10}$H$_{15}$—CH$_2$COOH) was obtained from Aldrich Chemical Co. Propionic acid was obtained from Matheson, Coleman & Bell.

Triethylamine (TEA) and N-methylmorpholine (NMM) were distilled from ninhydrin. Ethylenediamine (EDA) and n-butylamine were distilled from sodium. Ethanolamine was freshly distilled.

Acetic acid used as the HCl-acetic acid cleavage reagent was heated under reflux with boron triacetate and distilled from the reagent. Dimethylformamide (DMF) was distilled under reduced pressure immediately before use. Methanol was dried with magnesium methoxide and distilled. Other solvents and reagents were analytical grade.

Thin layer chromatography (TLC) was done on silica gel plates (0.25 mm, Brinkmann Silplate) using the following solvent systems:
CM: chloroform:methanol (7:3 v/v)
BAW: butan-1-ol:acetic acid:water (4:1:5 v/v, upper phase or 4:1:1 v/v)
BAWP: butan-1-ol:acetic acid: water:pyridine (15:3:3:10 v/v)
CMA: chloroform:methanol:acetic acid 17:2:1 v/v
EAP: ethanol:pyridine (0.1%): acetic acid (0.1%) (4:1:1 v/v)

The applied loadings were 10-50 micrograms. The minimum length of the chromatograms was 10 cm. Chloroplatinate reagent and iodine vapor were used for development of the chromatograms.

Amino acid analysis of the peptides was done by the method of Spackman et al., *Anal. Chem.*, vol. 30 (1958) at 1190, in which peptide samples weighing about 0.5 mg were hydrolyzed with constant boiling hydrochloric acid (400 microliters) in evacuated and sealed ampuoles for 18 h at 120° C. The analyses were performed using a Beckman Automatic Amino Acid Analyzer, Model 121. Molar ratios were referred to Gly, Arg or Phe=1.00. Elemental analyses were performed by Galbraith Laboratories, Inc., Knoxville, Tenn. The analytical results for the elements indicated by their respective symbols were within ±0.4% of theoretical values. Optical rotations were measured with a Rudolph Autopol III Polarimeter.

EXAMPLE 1 beta-(S-Benzylmercapto)-beta,beta-cyclopentamethylenepropionyl-Tyr(Me)-Phe-Gln-Asn-Cys(Bzl)-Pro-Arg(Tos)-GlyNH$_2$ (a) Combination of Solid Phase and Solution Methods.

Boc-Tyr(Me)-Phe-Gln-Asn-Cys(Bzl)-Pro-Arg(Tos)-GlyNH$_2$, prepared by the method of Bankowski et al., *J. Med. Chem.*, vol. 21 (1978) at 850 (319 mg, 0.26 mmol), was dissolved in CF$_3$COOH (6.5 ml) and stirred at room temperature for 40 mins. Cold ether (20 ml) was added to produce a precipitate, which was filtered and washed with ether (5 × 10 ml). The product was dried in vacuo over sodium hydroxide pellets. This material (318.5 mg) was dissolved in DMF (0.8 ml), to which was added N-methylmorpholine (10 microliters). The resulting solution had a pH of 7-8, measured with moist pH paper. After this neutralized solution was stirred at room temperature for 30 mins, a solution of p-nitrophenyl beta-(S-benzylmercapto)-beta,beta-cyclopentamethylenepropionate, Nestor et al., *J. Med. Chem.*, vol. 18 (1975) at 284, (445 mg, 1.155 mmol in 0.4 ml of DMF) was added. The reaction mixture was stirred at room temperature. After 72 hours' stirring, TLC analysis using system D showed that the reaction mixture still contained a trace of the free octapeptide amide. N-Hydroxybenzotriazole monohydrate, Konig et al., *Chem. Ber.*, vol. 103 (1970) at 788, (39.3 mg, 0.26 mmol) was added. Coupling was complete within 5 hours. The precipitate was filtered, washed with cold ethyl acetate (4 × 10 ml) and dried in vacuo. The crude product (339 mg) was twice reprecipitated from DMF-methanol to give the acylpeptide amide (295.2 mg, 77.3%): mp 209°-211° C., [α]$_D^{24}$ = −43.6° (c 0.5, DMF); R$_f$(BAW 4:1:5) 0.45, R$_f$(BAWP) 0.63 Anal. (C$_{73}$H$_{94}$O$_{14}$N$_{14}$S$_3$) C, H, N.

(b) Total Synthesis on Resin

Boc-Tyr(Me)-Phe-Gln-Asn-Cys(Bzl)-Pro-Arg(Tos)-Gly-resin (1.11 g, 0.4 mmol prepared from Boc-Gly-resin using solid phase methodology) was converted to the acyloctapeptide resin (1.167 g, weight gain 57 mg, 97.6% of theory) in one cycle of deprotection, neutralization and coupling with p-nitrophenyl beta-(S-benzylmercapto)-beta,beta-cyclopentamethylenepropionate, see Nestor, supra. The resin was ammonolyzed, Manning, *J. Am. Chem. Soc.*, vol. 90 (1968) at 1348. The product was extracted with DMF. After the solvent was evaporated in vacuo, the residue was precipitated by addition of water. The crude product (410 mg) was twice reprecipitated from DMF-ethanol to give the acyloctapeptide (302 mg, 50.7% based upon initial glycine content of the resin); mp 206°-208° C. (decomp);

R$_f$(BAW 4:1:5) 0.45; R$_f$(BAWP) 0.63; $[\alpha]_D^{24} = -43.1°$ (C=1, DMF). Anal. (C$_{73}$H$_{94}$N$_{14}$O$_{14}$S$_3$) C, H, N.

Amino acid analysis: Tyr, 0.79; Phe, 1.01; Glu, 1.03; Asp, 1.04; Cys(Bzl), 0.97; Pro, 1.03; Arg, 0.99; Gly, 1.00; NH$_3$, 2.95.

EXAMPLE 2 beta-(S-Benzylmercapto)-beta,beta-cyclopentamethylenepropionyl-Tyr(Bzl)-Phe-Gln-Asn-Cys(Bzl)-Pro-Arg(Tos)-GlyNH$_2$ Boc-Tyr(Bzl)-Phe-Gln-Asn-Cys(Bzl)-Pro-Arg(Tos)-Gly-resin (1.46 g, 0.5 mmol) was converted to the acyloctapeptide resin (1.55 g, weight gain 70 mg, 95.9% of theory) as in Example 1 by one cycle of deprotection, neutralization and coupling with p-nitrophenyl beta-(S-benzylmercapto)-beta,beta-cyclopentamethylenepropionate. The product obtained by ammonolysis of the resin was extracted with DMF. The solvent was evaporated in vacuo and the residue was precipitated by addition of water. The crude product (723 mg) was reprecipitated from DMF-ethanol and DMF-2% aqueous AcOH. Yield: 488 mg (62.4% based on initial Gly content on the resin); mp. 183°-185° C.; R$_f$(BAW 4:1:5) 0.38; R$_f$(CM) 0.41; $[\alpha]_D^{23} = -23.9°$ (C=1, DMF). Anal. (C$_{79}$H$_{98}$N$_{14}$O$_{14}$S$_3$) C, H, N.

Amino acid analysis: Tyr, 0.97; Phe, 1.02; Glu, 1.05; Asp, 1.01; Cys(Bzl), 0.98; Pro, 1.04; Arg, 0.98; Gly, 1.00; NH$_3$, 2.95.

EXAMPLE 3

(a) Aaa-D-Tyr(Et)-Phe-Val-Asn-Orn(Tos)-Pro-Arg(Tos)NH$_2$

A representative protected octapeptide intermediate is made, starting with 0.75 g (0.3 mmol) of BocArg-(Tos)-resin, which is suspended in methylene chloride overnight and coupled on the following day with Boc-Pro. The thus-produced dipeptide-resin is coupled with BocOrn(Tos), Boc-AsnONp, BocVal, BocPhe, Boc-D-Tyr(Et) and 1-adamantylacetic acid, respectively, by several cycles of deprotection, neutralization and coupling, to produce a protected octapeptide-resin. The resin (1.12 g) is subjected to ammonolysis.

Ammonia and methanol are removed from the ammonolysis product by evaporation. The ammonolysis residue is extracted with hot DMF (one 10-ml portion and three 8-ml portions). The peptide is precipitated from the combined extracts with hot water.

The yield of Aaa-D-Tyr(Et)-Phe-Val-Asn-Orn(Tos)-Pro-Arg(Tos)NH$_2$ is 248 mg (58.2%). Physical properties are given in Table 1A.

(b) Aaa-D-Tyr(Et)-Phe-Val-Asn-Orn-Pro-ArgNH$_2$

The product (120 mg, 0.0845 mmol) of Example 3(a) is subjected to reduction with sodium in liquid ammonia as described in Manning et al., U.S. Pat. No. 4,367,225.

After removal of ammonia from the crude product, the crude product is dissolved in about 15 ml of 50% acetic acid and applied to a column of Sephadex G-15. The material on the column is eluted with 50% acetic acid by the technique of Manning et al., *J. Chromatography*, vol. 58 (1968) at 396. The residues from evaporation of elution fluid from the contents of tubes 76-95 (80 mg) and tubes 96-104 (23 mg) by lyophilization, are collected. Additional product (3.5 mg) is obtained by lyophilization of the eluate in tubes 105-112.

TABLE 1A

Physiochemical Data for Protected Linear Octapeptides

| Potected Peptide | Yield (%) | M.p. (°C.) | $[\alpha]^{20}$ (C = 1%, D$_{DMF}$) | TLC (R$_f$) BAW 4:1:1 | BAWP 15:3:3:10 | CM 7:3 |
|---|---|---|---|---|---|---|
| Aaa-D-Tyr(Et)-Phe-Val-Asn-Abu-Pro-Arg(Tos)(NH$_2$) | 59.3 | 238-241 | −22.6 | 0.54 | 0.73 | 0.97 |
| Aaa-D-Tyr(Et)-Phe-Val-Asn-Orn(Tos)-Pro-Arg(Tos)(NH$_2$) | 58.2 | 234-237 | −19.3 | 0.55 | 0.71 | 0.74 |
| Aaa-D-Tyr(Et)-Phe-Val-Asn-Lys(Tos)-Pro-Arg(Tos)(NH$_2$) | 30.3 | 236-240 | −19.8 | 0.57 | 0.70 | 0.71 |
| Aaa-D-Tyr(Et)-Phe-Val-Asn-Arg(Tos)-Pro-Arg(Tos)(NH$_2$) | 47.3 | 216-219 | −15.5 | 0.56 | 0.70 | 0.65 |

$[\alpha]_D^{20} = -32.7°$ (C=0.1, 50% HOAc)

Other physicochemical data are given in Table 1B.

(c) Aaa-D-Tyr(Et)-Phe-Val-Asn-Abu-Pro-Arg(Tos)NH$_2$

Protected precursor, Aaa-D-Tyr(Et)-Phe-Val-Asn-Abu(Tos)-Pro-Arg(Tos)NH$_2$, is made as in Example 3(a). This material (1 g, about 0.3 mmol) is subjected to ammonolysis as in Example 3(a). The ammonolysis product is extracted with hot DMF and precipitated by addition of hot water. The yield is 220 mg (59.3%).

Physicochemical properties of the product are shown in Table 1A.

(d) Aaa-D-Tyr(Et)-Phe-Val-Asn-Abu-Pro-ArgNH$_2$

The protected octapeptide (100 mg) of Example 3(c) is reduced as in Example 3(b). After evaporation of ammonia from the reaction mixture, the crude product is put on a column as in Example 3(b). The contents of tubes 90-106 are collected and lyophilized to give 68 mg of octapeptide.

The octapeptide is applied to a second column of Sephadex G-15 and eluted with 0.2M acetic acid. The eluates in tubes 59-130 are collected and lyophilized. The yield is 31.5 mg (36%).

$[\alpha]_D^{20} = -60.0°$ (C=0.1, 50% HOAc)

Other physicochemical data are given in Table 1B.

In a similar manner are prepared compounds shown in Tables 1A and 1B.

EXAMPLE 4

(a) [1-(beta)-Mercapto-beta,beta-cyclopentamethylenepropionic acid), 2-substituted, 4-substituted, 9-desglycinamide]-arginine vasopressin derivatives Representative desglycinamide compounds are made as above, starting from Boc-Arg(Tos)-resin. The terminal arginine function is cleaved from the resin using a cleaving agent corresponding to QH in the structural formulas.

When Q is NH$_2$, cleavage from the resin is done with ammonia, in accordance with Manning et al., supra.

When Q is —NH(CH$_2$)$_p$NH$_2$, NH(CH$_2$)$_q$OH or alkNH$_2$, the product is cleaved from the resin by the method of Glass et al., supra., using an alkylene diamine, an alkanolamine or an alkylamine, respectively.

TABLE 1B

Physiochemical Data for Free Linear Octapeptides

| Structure | Yield, % | TLC ($R_f$) BAW 4:1:1 | BAWP |
|---|---|---|---|
| Aaa-D-Tyr(Et)-Phe-Val-Asn-Abu-Pro-Arg(NH$_2$) | 36.0 | 0.31 | 0.54 |
| Aaa-D-Tyr(Et)-Phe-Val-Asn-Orn-Pro-Arg(NH$_2$) | 85.1 | 0.14 | 0.37 |
| Aaa-D-Tyr(Et)-Phe-Val-Asn-Lys-Pro-Arg(NH$_2$) | 40.2 | 0.04 | 0.27 |
| Aaa-D-Tyr(Et)-Phe-Val-Asn-Arg-Pro-Arg(NH$_2$) | 54.6 | 0.18 | 0.46 |

(i) Cleavage with ethanolamine

A representative protected peptidyl resin, beta-(S-benzylmercapto)-beta, beta-cyclopentamethylenepropionyl-D-Tyr(Et)-Phe-Ile-Asn-Cys(Bzl)-Pro-Arg(Tos)-resin (3 g, about 0.75 mmol) was suspended in 15 ml of anhydrous methanol and 15 ml of freshly-distilled ethanolamine (bp above 171° C.) and stirred at room temperature for four days. Following removal of the solvents, the residue was extracted with hot DMF and reprecipitated with 1 L of water and with DMF/ether to give 640 mg of product. The uncyclized product was characterized by TLC, as follows:
BAW (4:1:5): 0.82
CHCl$_3$:MeOH (9:1): 0.25

The product (120 mg) was cyclized and purified as described in the foregoing examples to give the free peptide, [1-(beta-mercapto-beta,beta-cyclopentamethylenepropionic acid), 2-D-(O-ethyl)tyrosine, 4-isoleucine, 8-arginine-N-(beta-hydroxy)ethylamide, 9-desglycinamide]-arginine vasopressin. The yield was 15.5 mg (13.4%).

(b) [1-(beta-(Mercapto)-beta,beta-cyclopentamethylenepropionic acid), 2-substituted, 4-substituted, 9-modified]-arginine vasopressin Compounds are prepared as above. A protected nonapeptide is cleaved from the resin with an agent, corresponding to QH in the formulas, by methods outlined in Example 4(a). Alternatively, the compounds can be made by 8+1 coupling in solution.

(i) Cleavage with methylamine

Protected peptidyl resin, beta-(S-benzylmercapto)-beta,beta-cyclopentamethylenepropionyl-D-Tyr(Et)-Phe-Val-Asn-Cys(Bzl)-Pro-Arg(Tos)-Gly-resin (3.02 g, 1 mmol), was suspended in 50 ml of dry methanol. Methylamine was bubbled through the suspension until the volume increased by about 10 ml. The flask was stoppered and stirred at room temperature for 72 h, after which solvents were removed by evaporation. The product was extracted with hot DMF (3×25 ml portions) and precipitated by addition of 1 L of water. The product weighed 2.53 g and was reprecipitated from DMF-ethanol and DMF-ethanol-ether to give 1.03 g (69.3%), of uncyclized peptide, mp 180°–182° C.

The intermediate (150 mg) was reduced with sodium in liquid ammonia, reoxidized, deionized and purified as above to give 45 mg (38.7%) of d(CH$_2$)$_5$[D-Tyr(Et)$^2$, Val$^4$, GlyNHMe$^9$]AVP.

(ii) Cleavage with n-butylamine

Protected peptidyl resin, beta-(S-benzylmercapto)-beta,beta-cyclopentamethylenepropionyl-Tyr(Me)-Phe-Gln-Asn-Cys(Bzl)-Pro-Arg(Tos)-Gly-resin (2.0 g), was suspended in 10 ml of anhydrous methanol and 20 ml of n-butylamine, freshly distilled from sodium, and the resulting mixture was stirred at room temperature for 4 days. The solvents were removed by evaporation. The residue was extracted with DMF. The product was precipitated from the DMF solution with water, dried and reprecipitated from DMF with ethanol/ether to give the protected intermediate, having the terminal sequence -Pro-Arg(Tos)-GlyNHC$_4$H$_9$-n, $[\alpha]_D^{24} = -34°$ (C=1, DMF).

The intermediate had the following $R_f$ by TLC:
BAW (4:1:5): 0.76
BAWP: 0.88
CHCl$_3$:MeOH (9:1): 0.73

The intermediate (150 mg) was deblocked with sodium in liquid ammonia and purified as above to give 55 mg (48.3%) of the cyclized free peptide, d(CH$_2$)$_5$[Tyr(Me)$^2$, GlyNHBu-n$^9$]AVP, $[\alpha]_D^{24} = -43.3°$ (C=0.3, 1N HOAc)

(iii) [1-(beta-mercapto-beta,beta-cyclopentamethylenepropionic acid), 2-D-(O-ethyl)tyrosine, 4-valine, 9-beta-alanine-N-methylamide]-arginine vasopressin by 8+1 solution synthesis Protected acyloctapeptide, beta-(S-benzylmercapto)-beta,beta-cyclopentamethylenepropionyl-D-Tyr(Et)-Phe-Val-Asn-Cys(Bzl)-Pro-Arg(Tos) (442.1 mg, 0.3 mmol), obtained by cleavage of protected peptidyl resin with HBr/TFA as described by Walter et al., supra, was coupled with beta-alanine-N-methylamide hydrochloride (166.3 mg, 1.2 mmol), to give the protected intermediate, terminated with a beta-alanine-N-methylamide moiety. The product weighed 361.7 mg (50.1%), mp 195°–200° C.

TLC had the following $R_f$ values:
CHCl$_3$:MeOH (9:1): 0.73
BAW (4:1:5): 0.74
BAWP: 0.79

The blocking groups were removed, after which the deblocked material was reoxidized, deionized and purified as above to give the free peptide in 35.4 mg (30.4%) yield. $[\alpha]_D^{28} = -51.3°$ (C=0.3, 1N HOAc).

TABLE 2A

Physiochemical Data for Protected Linear Nonapeptides

| Protected Peptides | Yield (%) | M.p. (°C.) | TLC ($R_f$) BAW 4:1:1 | BAWP 15:3:3:10 | CM 7:3 | BAW 4:1:5 | CMA 17:2:1 |
|---|---|---|---|---|---|---|---|
| d(CH$_2$)$_5$(S-Bzl)-D-Tyr(Et)-Phe-Val-Asn-Cys(Bzl)-Pro-Arg(Tos)-Gly(NH$_2$)$^+$ | 98.3 | 208–210 | 0.57 | 0.82 | 0.73 | | |
| d(CH$_2$)$_5$(S-Bzl)-D-Tyr(Et)-Phe-Val-Asn-Abu-Pro-Arg(Tos)-Gly(NH$_2$) | 83.4 | 219–221 | 0.61 | 0.82 | 0.70 | 0.51 | |
| d(Et$_2$)(S-Bzl)-D-Tyr(Et)-Phe-Val-Asn-Abu-Pro-Arg(Tos)-Gly(HN$_2$) | 100 | 213–216 | 0.48 | 0.67 | | 0.47 | |
| Aaa-D-Tyr(Et)-Phe-Val-Asn-Abu-Pro-Arg(Tos)-Gly(NH$_2$) | 88.7 | 231–235 | 0.68 | 0.86 | 0.73 | 0.57 | |
| Aaa-D-Tyr(Et)-Phe-Val-Asn-Abu-Pro-Arg(Tos)-NH(CH$_2$)$_2$NH$_2$ | 69.8 | 224–228 decomp. | 0.39 | 0.60 | | | |

TABLE 2A-continued

Physiochemical Data for Protected Linear Nonapeptides

| Protected Peptides | Yield (%) | M.p. (°C.) | TLC ($R_f$) BAW 4:1:1 | BAWP 15:3:3:10 | CM 7:3 | BAW 4:1:5 | CMA 17:2:1 |
|---|---|---|---|---|---|---|---|
| Aaa-D-Tyr(Et)-Phe-Val-Asn-Abu-Pro-Arg(Tos)-Ala(NH₂) | 85.6 | 242–244 | 0.66 | 0.69 | | | 0.20 |
| Aaa-D-Tyr(Et)-Phe-Val-Asn-Abu-Pro-Arg(Tos)-Arg(Tos)(NH₂) | 73.7 | 210–212 | 0.59 | 0.72 | | | 0.14 |
| Aaa-D-Tyr(Et)-Phe-Val-Asn-Abu-Pro-D-Arg(Tos)-Arg(Tos(NH₂) | 65.7 | 201–204 | 0.61 | 0.69 | 0.78 | | |
| Pa-D-Tyr(Et)-Phe-Val-Asn-Abu-Pro-Arg(Tos)-Arg(Tos)(NH₂) | 55.6 | 220–223 | 0.53 | 0.69 | 0.81 | | |

+ Protected precursor of cyclic d(CH₂)₅D-Tyr(Et)VAVP. Manning et al. J. Med. Chem., vol. 25 (1982), page 45.

TABLE 2B

Physiochemical Data for Free Linear Nonapeptides

| Structure | Yield, % | TLC ($R_f$) BAW 4:1:1 | BAW 4:1:5 | BAWP |
|---|---|---|---|---|
| d(CH₂)₅(SH)-D-Tyr(Et)-Phe-Val-Asn-Cys(SH)-Pro-Arg-Gly(NH₂) | 51.2 | 0.29 | 0.33 | 0.75 |
| d(CH₂)₅(SH)-D-Tyr(Et)-Phe-Val-Asn-Abu-Pro-Arg-Gly(NH₂) | 63.7 | 0.35 | 0.32 | 0.75 |
| d(Et)₂(SH)-D-Tyr(Et)-Phe-Val-Abu-Pro-Arg-Gly(NH₂) | 82.3 | 0.31 | 0.31 | 0.60 |
| Aaa-D-Tyr(Et)-Phe-Val-Asn-Abu-Pro-Arg-Gly(NH₂) | 76.6 | 0.35 | 0.31 | 0.75 |
| Aaa-D-Tyr(Et)-Phe-Val-Asn-Abu-Pro-Arg-Eda | 53.5 | 0.12 | — | 0.34 |
| Aaa-D-Tyr(Et)-Phe-Val-Asn-Abu-Pro-Arg-Ala(NH₂) | 82.1 | 0.32 | — | 0.64 |
| Aaa-D-Tyr(Et)-Phe-Val-Asn-Abu-Pro-Arg-Arg(NH₂) | 50.5 | 0.14 | — | 0.46 |
| Aaa-D-Tyr(Et)-Phe-Val-Asn-Abu-Pro-D-Arg-Arg(NH₂) | 64.2 | 0.06 | — | 0.28 |
| Pa-D-Tyr(Et)-Phe-Val-Asn-Abu-Pro-Arg-Arg(NH₂) | 73.9 | 0.04 | — | 0.26 |

EXAMPLE 5

(a) Aaa-D-Tyr(Et)-Phe-Val-Asn-Abu-Pro-Arg(Tos)-NHCH₂CH₂NH₂

Protected resin (1 g, about 0.3 mmol), made as in Examples 3(a) or 3(c), is suspended in 50 ml of methanol and 20 ml of ethylene diamine. The mixture is cooled and stirred for about 65 h. Excess ethylene diamine and methanol are removed by evaporation. The peptide is extracted with hot DMF and precipitated by addition of hot water. The yield of crude material is 290 mg. The peptide is reprecipitated from 5 ml of DMF, 20 ml of EtOH and 300 ml of ether to give 268 mg (69.7%) of product.

$R_f$(EAP) 0.77

$[\alpha]_D^{20} = -21.9°$ (C=0.7, DMF)

Other physicochemical properties are given in Table 2A.

(b) Aaa-D-Tyr(Et)-Phe-Val-Asn-Abu-Arg-NHCH₂CH₂NH₂

The compound of Example 5(a) (120 mg, 0.0937 mmol) is reduced as in the foregoing examples. The crude product is applied to a column as in Example 3. The contents of tubes 90–104 are collected and lyophilized to give 70 mg of peptide. This material is applied to a second column. The contents of tubes 43–60 are collected and lyophilized to give 56.5 mg (53.5%) of peptide.

$[\alpha]_D^{20} = -56.4°$ (C=0.1, 50% HOAc)

Other physicochemical properties are shown in Table 2B. In addition to the TLC data presented in the table, the chromatogram in BAWP had a very small additional spot at 0.40 and the chromatogram in BAW (4:1:1) had three additional small spots at 0.06, 0.18 and 0.021.

EXAMPLE 6

(a) Aaa-D-Tyr(Et)-Phe-Val-Asn-Abu-Pro-Arg(Tos)OH

Protected octapeptide resin (4.5 g, about 1.4 mmol), made as in Example 3(a) or 3(c), is suspended in 30 ml of TFA containing 5 ml of anisole in accordance with Walter et al. Hydrogen bromide is bubbled into the resulting suspension slowly for 1 h. Solvent is removed from the suspension by filtration. The residual peptide-resin is suspended in 30 ml of TFA:methylene chloride (1:1 v/v) and 3 ml of anisole. The cleavage reaction is repeated for 30 min. Solvent is removed by filtration and the residual resin is washed twice with 1:1 TFA:-methylene chloride. The combined filtrates and washings are evaporated to dryness. Ether is added to the residue. The crude peptide is reprecipitated from DMF-water.

Yield: 868.3 mg (50.2%)

| $R_f$ | BAW | 0.52 |
|---|---|---|
| | BAWP | 0.64 |
| | CM | 0.38 | mp, 211°–213° C.

$[\alpha]_D^{20} = -20.0°$ (C=0.7, DMF).

(b) Aaa-D-Tyr(Et)-Phe-Val-Asn-Abu-Pro-Arg(Tos)AlaNH₂

Protected octapeptide acid of Example 6(a) (433 mg, 0.35 mmol), 130.3 mg (1.05 mmol) of alaninamide hydrochloride and 142 mg (1.05 mmol) of N-hydroxybenzotriazole are dissolved in 5 ml of DMF. To this mixture is added 0.115 ml of N-methylmorpholine. The resulting mixture is cooled to −10° C. and 72 mg (0.35 mmol) of dicyclohexyl carbodiimide is added. The resulting mixture is stirred for 4 days.

The resulting mixture is filtered to remove dicyclohexyl urea. The residue on the filter is washed with about 1 ml of DMF. The crude peptide is precipitated from the combined filtrate and washings by addition of ether. The crude peptide is washed with 0.5N HCl, water, 5% sodium bicarbonate, and water and dried. The peptide is reprecipitated from 6 ml of HOAc, 20 ml of EtOH and 100 ml of ether. The yield is 410 mg.

This material contains traces of the 8-peptide acid, which is removed by washing with 5% sodium bicarbonate solution and water. The peptide is washed with ether and dried.

$[\alpha]_D^{20} = -18.6°$ (C=1, DMF)

Other physicochemical properties are given in Table 2A.

(c) Aaa-D-Tyr(Et)-Phe-Val-Asn-Abu-Pro-Arg-AlaNH$_2$

The protected nonapeptide of Example 6(b) (100 mg, 0.076 mmol) is subjected to reduction as in the foregoing examples. After removal of ammonia, the product is applied to a chromatography column as in Example 3(b). The material in tubes 97–106 is collected and lyophilized. Material in tubes 107–110 is collected separately and lyophilized. The combined materials weigh 72 mg (82%)

$[\alpha]_D^{20} = -55.8°$ (C=0.1, 50% HOAc)
R$_f$(EAP) 0.87

Other physicochemical properties are given in Table 2B.

(d) Aaa-D-Tyr(Et)-Phe-Val-Asn-Abu-Pro-Arg(Tos)-Arg(Tos)NH$_2$

The acid of Example 6(a) (402 mg, 0.32 mmol), tosyl-arginamide hydrochloride (371 mg, 0.96 mmol), and 130 mg of N-hydroxybenzotriazole are dissolved in 5 ml of DMF, to which is added 0.105 ml of N-methylmorpholine. The resulting mixture is cooled to −10° C. and dicyclohexyl carbodiimide (66 mg, 0.32 mmol) is added. The mixture is stirred for three days, after which dicyclohexyl urea is removed by filtration. The residue on the filtrate is washed with DMF and peptide is precipitated from the combined filtrate and washings by addition of ether.

Crude peptide is filtered and washed with 0.5N HCl, water, 5% sodium bicarbonate solution, and water and dried. This material contains octapeptide. Washing with 5% NaOH, water, ethanol-ether and ether, followed by drying, removes most of the octapeptide.

$[\alpha]_D^{20} = -15.7°$ (C=0.8, DMF).

Other physicochemical properties are given in Table 2A.

(e) Aaa-D-Tyr(Et)-Phe-Val-Asn-Abu-Pro-Arg-ArgNH$_2$

Protected peptide of Example 6(d) (120 mg, 0.0775 mmol) is reduced as in the foregoing examples. The product in tubes 69–78 of the chromatography eluate is collected and lyophilized.

$[\alpha]_D^{20} = -51.7°$ (C=0.27, 50% HOAc).

Other physicochemical properties are given in Table 2B.

(f) Pa-D-Tyr(Et)-Phe-Val-Asn-Abu-Pro-Arg(Tos)-Arg(Tos)NH$_2$

The protected precursor, Pa-D-Tyr(Et)-Phe-Val-Asn-Abu-Pro-Arg(Tos)-Arg-(Tos)NH$_2$ is made as in Examples 3(a) or 3(c), except that an additional Boc-Arg-(Tos) is incorporated in the peptide chain before the Boc-Pro unit and propionic acid is used instead of 1-adamantylacetic acid in the final coupling step. The protected nonapeptide resin (1.73 g) is subjected to ammonolysis as in Example 3(b). The ammonolysis product is extracted with hot DMF and precipitated by the addition of hot water.

The yield is 313.6 mg (55.6%). Physicochemical properties are given in Table 2A.

(g) Pa-D-Tyr(Et)-Phe-Val-Asn-Abu-Pro-Arg-ArgNH$_2$

The protected nonapeptide (100 mg) of Example 6(f) is reduced with sodium in liquid ammonia as in Example 3(b). After evaporation of the ammonia from the reaction mixture, the crude product is put on a column as in Example 3(b).

The contents of tubes 54–62 are collected and lyophilized to give 57.6 mg (73.9%) of free nonapeptide.

Other compounds, for which physicochemical properties are presented in Tables 2A and 2B, are prepared using the foregoing procedures.

EXAMPLE 7

Antagonism to the vasopressor response was estimated in accordance with Dyckes et al., *J. Med. Chem.*, vol. 17 (1974) at 969. The values are expressed as pA$_2$ values, defined as in Schild et al., *Br. J. Pharmacol.*, vol. 2 (1947) at 189.

Activity as antidiuretic agonists was determined by intravenous injection of the compounds being evaluated in ethanol-anesthesized water-loaded rats in accordance with Sawyer, *Endocrinology*, vol. 63 (1958) at 694. Antagonism of the antidiuretic response to subsequent injections of arginine vasopressin was tested by the method of Sawyer et al., *Science*, vol. 212 (1981) at 49.

Antagonistic potencies were determined and expressed as "effective doses" and pA$_2$ values. The "effective dose" is defined as the dose (in nanomoles per kilogram) that reduces the response seen from 2x units of agonist injected 20 min after the dose of antagonist to the response with 1x units of agonist. Estimated in vivo "pA$_2$" values represent the negative logarithms of the effective doses, divided by the estimated volume of distribution (67 ml/kg). Results are given in Tables 3A and 3B.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

TABLE 3A

Linear Octapeptide Vasopressin Antagonists

| | Antiantidiuretic | | Antivasopressor | | |
|---|---|---|---|---|---|
| | ED (nmoles/Kg) | pA$_2$ | ED (nmoles/Kg) | pA$_2$ | Selectivity AD/VP |
| Aaa-D-Tyr(Et)-Phe-Val-Asn-Abu-Pro-Arg-(NH$_2$) | 4.2 ± 0.4 | 7.20 ± 0.04 | 2.6 ± 0.3 | 7.43 ± 0.06 | 0.6 |
| Aaa-D-Tyr(Et)-Phe-Val-Asn-Orn-Pro-Arg-(NH$_2$) | 1.1 ± 0.3 | 7.81 ± 0.10 | 3.2 ± 0.5 | 7.33 ± 0.06 | 2.9 |
| Aaa-D-Tyr(Et)-Phe-Val-Asn-Lys-Pro-Arg-(NH$_2$) | 1.1 ± 0.2 | 7.81 ± 0.08 | 0.66 ± 0.09 | 8.02 ± 0.06 | 0.6 |
| Aaa-D-Tyr(Et)-Phe-Val-Asn-Arg-Pro-Arg-(NH$_2$) | 1.4 ± 0.3 | 7.73 ± 0.08 | 0.66 ± 0.07 | 8.01 ± 0.05 | 0.5 |

TABLE 3B

| Linear Nonapeptide Vasopressin Antagonists | | | | | |
|---|---|---|---|---|---|
| | Antiantidiuretic | | Antivasopressor | | |
| | ED (nmoles/Kg) | $pA_2$ | ED (nmoles/Kg) | $pA_2$ | Selectivity AD/VP |
| $d(CH_2)_5(SH)$-D-Tyr(Et)-Phe-Val-Asn-Cy(SH)-Pro-Arg-Gly(NH$_2$) | 6.2 ± 1.1 | 7.05 ± 0.08 | 2.1 ± 0.2 | 7.51 ± 0.03 | 0.3 |
| $d(CH_2)_5(SH)$-D-Tyr(Et)-Phe-Val-Asn-Abu-Pro-Arg-Gly(NH$_2$) | 2.6 ± 0.3 | 7.42 ± 0.05 | 1.3 ± 0.2 | 7.71 ± 0.05 | 0.5 |
| dEt$_2$(SH)-D-Tyr(Et)-Phe-Val-Asn-Abu-Pro-Arg-Gly(NH$_2$) | 6.1 ± 0.9 | 7.09 ± 0.09 | 7.8 ± 0.8 | 6.94 ± 0.04 | 1.3 |
| Aaa-D-Tyr(Et)-Phe-Val-Asn-Abu-Pro-Arg-Gly(NH$_2$) | 2.1 ± 0.1 | 7.50 ± 0.02 | 5.7 ± 0.9 | 7.10 ± 0.07 | 2.7 |
| Aaa-D-Tyr(Et)-Phe-Val-Asn-Abu-Pro-Arg-Eda | 1.4 ± 0.3 | 7.71 ± 0.09 | 3.3 ± 0.6 | 7.33 ± 0.09 | 2.4 |
| Aaa-D-Tyr(Et)-Phe-Val-Asn-Abu-Pro-Arg-Ala(NH$_2$) | 19 ± 2 | 6.55 ± 0.04 | 4.5 ± 0.4 | 7.18 ± 0.04 | 0.2 |
| Aaa-D-Tyr(Et)-Phe-Val-Asn-Abu-Pro-Arg-Arg(NH$_2$) | 0.53 ± 0.07 | 8.11 ± 0.07 | 1.2 ± 0.2 | 7.75 ± 0.07 | 2.3 |
| Aaa-D-Tyr(Et)-Phe-Val-Asn-Abu-Pro-D-Arg-Arg(NH$_2$) | 1.0 ± 0.2 | 7.85 ± 0.08 | 2.2 ± 0.3 | 7.49 ± 0.06 | 2.2 |
| Pa-D-Tyr(Et)-Phe-Val-Asn-Abu-Pro-Arg-Arg(NH$_2$) | 1.3 ± 0.2 | 7.74 ± 0.07 | 14 ± 3 | 6.71 ± 0.09 | 11 |

We claim:

1. (1-Adamantyl)acetyl-D-(O-ethyl)tyrosyl-phenylalanyl-valyl-asparaginyl-(2-amino)butyryl-prolyl-argininamide.

2. (1-Adamantyl)acetyl-D-(O-ethyl)tyrosyl-phenylalanyl-valyl-asparaginyl-ornithyl-prolyl-argininamide.

3. (1-Adamantyl)acetyl-D-(O-ethyl)tyrosyl-phenylalanyl-valyl-asparaginyl-lysyl-prolyl-argininamide.

4. (1-Adamantyl)acetyl-D-(O-ethyl)tyrosyl-phenylalanyl-valyl-asparaginyl-arginyl-prolyl-argininamide.

5. (1-Adamantyl)acetyl-D-(O-ethyl)tyrosyl-phenylalanyl-valyl-asparaginyl-(2-amino)butyryl-prolyl-arginine-N-(2-amino ethyl)amide.

6. (1-Adamantyl)acetyl-D-(O-ethyl)tyrosyl-phenylalanyl-valyl-asparaginyl-(2-amino)butyryl-prolyl-arginyl-glycinamide.

7. (1-Adamantyl)acetyl-D-(O-ethyl)tyrosyl-phenylalanyl-valyl-asparaginyl-(2-amino)butyryl-prolyl-arginyl-alaninamide.

8. (1-Adamantyl)acetyl-D-(O-ethyl)tyrosyl-phenylalanyl-valyl-asparaginyl-(2-amino)butyryl-prolyl-arginyl-argininamide.

9. (1-Adamantyl)acetyl-D-(O-ethyl)tyrosyl-phenylalanyl-valyl-asparaginyl-(2-amino)butyryl-prolyl-D-arginyl-argininamide.

10. A method for antagonizing the in vivo response of an animal to the antidiuretic and/or vasopressor action of an antidiuretic hormone, comprising administering to the animal an amount of a compound of claim 2, in admixture with a physiologically and pharmaceutically acceptable carrier, effective to antagonize the antidiuretic and/or vasopressor responses to the antidiuretic hormone.

11. A method for antagonizing the in vivo response of an animal to the antidiuretic and/or vasopressor action of an antidiuretic hormone, comprising administering to the animal an amount of a compound of claim 3, in admixture with a physiologically and pharmaceutically acceptable carrier, effective to antagonize the antidiuretic and/or vasopressor responses to the antidiuretic hormone.

12. A method for antagonizing the in vivo response of an animal to the antidiuretic and/or vasopressor action of an antidiuretic hormone, comprising administering to the animal an amount of a compound of claim 4, in admixture with a physiologically and pharmaceutically acceptable carrier, effective to antagonize the antidiuretic and/or vasopressor responses to the antidiuretic hormone.

13. A method for antagonizing the in vivo response of an animal to the antidiuretic and/or vasopressor action of an antidiuretic hormone, comprising administering to the animal an amount of a compound of claim 5, in admixture with a physiologically and pharmaceutically acceptable carrier, effective to antagonize the antidiuretic and/or vasopressor responses to the antidiuretic hormone.

14. A method for antagonizing the in vivo response of an animal to the antidiuretic and/or vasopressor action of an antidiuretic hormone, comprising administering to the animal an amount of a compound of claim 8, in admixture with a physiologically and pharmaceutically acceptable carrier, effective to antagonize the antidiuretic and/or vasopressor responses to the antidiuretic hormone.

15. A method for antagonizing the in vivo response of an animal to the antidiuretic and/or vasopressor action of an antidiuretic hormone, comprising administering to the animal an amount of a compound of claim 9, in admixture with a physiologically and pharmaceutically acceptable carrier, effective to antagonize the antidiuretic and/or vasopressor responses to the antidiuretic hormone.

* * * * *